US012064609B2

(12) United States Patent
Madin et al.

(10) Patent No.: US 12,064,609 B2
(45) Date of Patent: Aug. 20, 2024

(54) NEEDLESTICK PREVENTION DEVICE

(71) Applicant: STAR SYRINGE LIMITED, London (GB)

(72) Inventors: Graham John Madin, Mielkendorf (DE); Steffen Kramer, Jevenstedt (DE); Norbert Rudolf, Neumunster (DE)

(73) Assignee: STAR SYRINGE LIMITED, London (GB)

( * ) Notice: Subject to any disclaimer, the term of this patent is extended or adjusted under 35 U.S.C. 154(b) by 44 days.

(21) Appl. No.: 16/469,544

(22) PCT Filed: Dec. 13, 2017

(86) PCT No.: PCT/GB2017/053733
§ 371 (c)(1),
(2) Date: Jun. 13, 2019

(87) PCT Pub. No.: WO2018/109470
PCT Pub. Date: Jun. 21, 2018

(65) Prior Publication Data
US 2020/0078532 A1 Mar. 12, 2020

(30) Foreign Application Priority Data

Dec. 14, 2016 (GB) ...................................... 1621266
Jan. 24, 2017 (PK) ...................................... 49/2017

(51) Int. Cl.
*A61M 5/32* (2006.01)
(52) U.S. Cl.
CPC ........ *A61M 5/3216* (2013.01); *A61M 5/3272* (2013.01); *A61M 2005/3217* (2013.01)
(58) Field of Classification Search
CPC .............. A61M 25/02; A61M 25/0618; A61M 5/3216; A61M 25/0631; A61M 25/0637;
(Continued)

(56) References Cited

U.S. PATENT DOCUMENTS 4,664,259 A * 5/1987 Landis ................ A61M 5/3216
  206/370
4,872,552 A * 10/1989 Unger ................. A61M 5/3202
  604/110

(Continued)

FOREIGN PATENT DOCUMENTS

EP 0832660 A2 4/1998
EP 2949355 A1 12/2015
(Continued)

OTHER PUBLICATIONS

International Search Report and Written Opinion for Application No. PCT/GB2017/053733, dated Jun. 20, 2018, 17 pages.

*Primary Examiner* — Scott J Medway
(74) *Attorney, Agent, or Firm* — Michael Best & Friedrich LLP

(57) ABSTRACT

A needlestick prevention device (100) for an injection needle carried by a needle-bearing member (101) of a syringe (102) is formed as a one-piece moulding and comprises a first part (103) adapted to be attached to the needle-bearing member (101) and a second part (104) providing a shield for the needle and pivotally movable relative to the first part to expose the needle for use. The device is adapted to adopt a first position in which the needle is protected for transport of the device prior to use, a second position in which the needle is exposed for filling of the syringe and injection, a third position in which the needle is protected after filling of the syringe but before injection and a fourth position in which the needle is locked in the device following injection. In one embodiment the shield (104) has a transport recess (124) and a locking recess (125) connected by a gate device (126), the arrangement being such that in the third position the needle (130) is in the transport recess (124) and is able to move into the second position, and in the fourth position the needle moves through the gate device (Continued)

(126) into the locking recess (125), with the gate device (126) preventing movement out of the fourth position. The device also includes energy-dissipating bumps (155) operative to reduce the energy of the shield (104) as it is returned to the third position and before the gate device contacts the needle (130) in order to prevent splattering of any liquid on the needle (130) out of the device.

19 Claims, 9 Drawing Sheets

(58) Field of Classification Search
CPC ...... A61M 25/3217; A61M 2205/6081; A61M 2005/158; A61M 25/0606; A61B 5/153; A61B 5/15003; A61B 5/150389; A61B 5/150503; A61B 5/150679
See application file for complete search history.

(56) References Cited

U.S. PATENT DOCUMENTS

| | | | | |
|---|---|---|---|---|
| 4,947,863 A * | 8/1990 | Haber | A61B 5/15003 600/577 |
| 4,976,699 A * | 12/1990 | Gold | A61M 5/3202 604/192 |
| 4,982,842 A * | 1/1991 | Hollister | A61M 5/3216 206/365 |
| 5,135,509 A * | 8/1992 | Olliffe | A61M 5/3216 604/263 |
| 5,151,089 A * | 9/1992 | Kirk, III | A61M 5/3216 604/192 |
| 5,242,417 A * | 9/1993 | Paudler | A61M 5/3216 206/365 |
| 5,312,359 A | 5/1994 | Wallace | |
| 5,312,369 A * | 5/1994 | Arcusin | A61M 5/3216 604/192 |
| 5,490,841 A | 2/1996 | Landis | |
| 5,632,732 A | 5/1997 | Szabo et al. | |
| 5,662,617 A * | 9/1997 | Odell | A61M 5/3216 128/919 |
| 5,669,889 A * | 9/1997 | Gyure | A61M 5/3216 128/919 |
| 5,681,295 A * | 10/1997 | Gyure | A61M 5/3202 604/263 |
| 5,693,022 A * | 12/1997 | Haynes | A61M 5/3216 604/192 |
| 5,733,265 A * | 3/1998 | Bachman | A61M 5/3216 604/192 |
| 6,334,857 B1 | 1/2002 | Hollister et al. | |
| 6,551,287 B2 | 4/2003 | Hollister et al. | |
| 6,695,819 B2 * | 2/2004 | Kobayashi | A61M 5/3216 604/192 |
| 6,752,788 B2 * | 6/2004 | Tuen | A61M 5/3216 604/110 |
| 7,163,526 B2 * | 1/2007 | Leong | A61B 5/1545 600/573 |
| 7,201,736 B2 * | 4/2007 | Hauri | A61M 5/3216 604/110 |
| 7,223,258 B2 * | 5/2007 | Crawford | A61M 5/002 604/110 |
| 7,635,352 B2 * | 12/2009 | Adams | A61M 25/0618 604/164.08 |
| 8,038,654 B2 * | 10/2011 | Lim | A61M 5/3216 604/192 |
| 8,057,431 B2 * | 11/2011 | Woehr | A61M 5/3216 604/110 |
| 8,226,576 B2 * | 7/2012 | Swenson | A61B 5/150473 600/576 |
| 8,251,961 B2 * | 8/2012 | Hauri | A61M 5/3202 604/263 |
| 8,801,672 B2 * | 8/2014 | Nagy | A61M 5/3216 604/192 |
| 10,029,049 B2 * | 7/2018 | Bubenik | A61M 5/3202 |
| 10,537,687 B2 * | 1/2020 | Lin | A61B 5/153 |
| 11,324,928 B2 * | 5/2022 | Knutsson | A61M 25/0631 |
| 2002/0099342 A1 * | 7/2002 | Zurcher | A61B 5/150503 604/272 |
| 2003/0187399 A1 * | 10/2003 | Crawford | A61B 5/15003 604/192 |
| 2005/0004531 A1 * | 1/2005 | Hwang | A61M 5/3216 604/263 |
| 2005/0015054 A1 | 1/2005 | Chen | |
| 2005/0124944 A1 * | 6/2005 | Hwang | A61M 5/3216 604/263 |
| 2006/0200078 A1 * | 9/2006 | Konrad | A61B 5/150671 604/110 |
| 2007/0088261 A1 | 4/2007 | Lew et al. | |
| 2008/0208138 A1 * | 8/2008 | Lim | A61M 5/3216 604/192 |
| 2009/0018510 A1 * | 1/2009 | Madin | A61M 5/3216 604/192 |
| 2012/0029441 A1 | 2/2012 | Madin et al. | |
| 2012/0323216 A1 | 12/2012 | Koh | |
| 2014/0008345 A1 | 1/2014 | Cheng | |
| 2014/0135713 A1 | 5/2014 | Domonkos | |
| 2015/0367104 A1 * | 12/2015 | Knutsson | A61M 25/0618 604/177 |
| 2016/0220766 A1 | 8/2016 | Kawano et al. | |

FOREIGN PATENT DOCUMENTS

| | | |
|---|---|---|
| JP | H06-58808 A | 3/1994 |
| TW | M436461 B | 5/2001 |
| TW | M485736 U | 9/2014 |
| WO | 2005023329 A2 | 3/2005 |
| WO | 2010059345 A2 | 5/2010 |
| WO | 2012152207 A1 | 11/2012 |
| WO | 2013029529 A1 | 3/2013 |

* cited by examiner

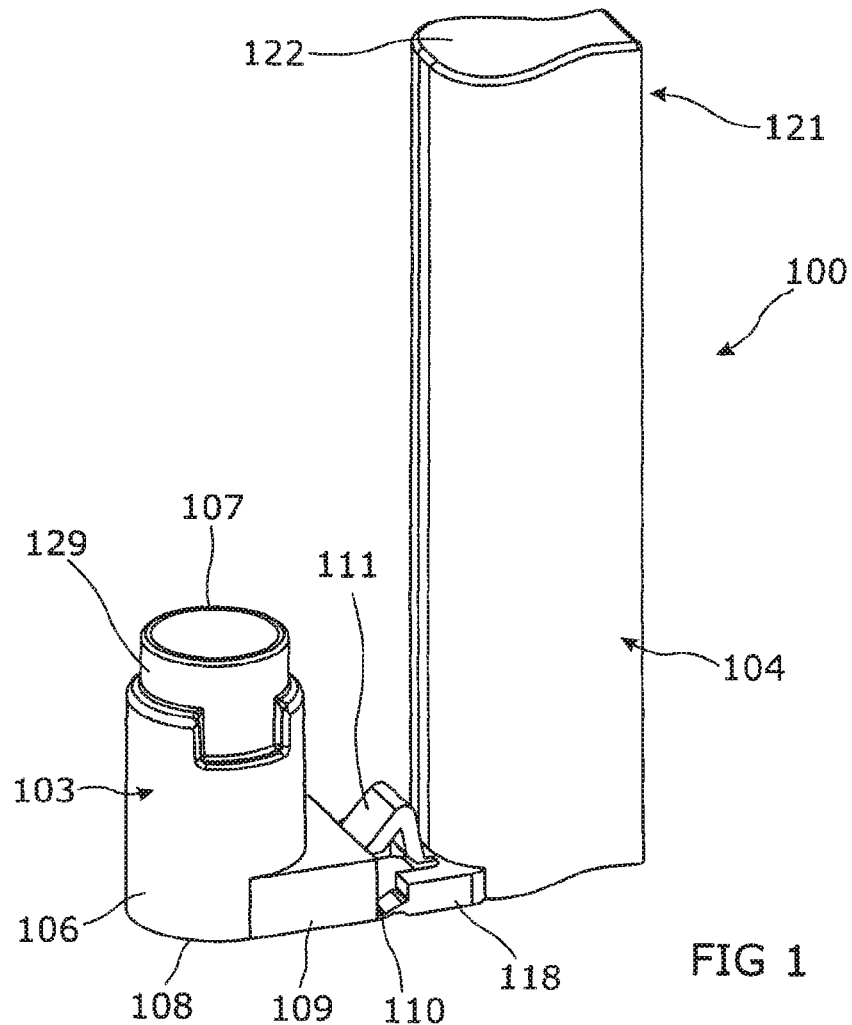
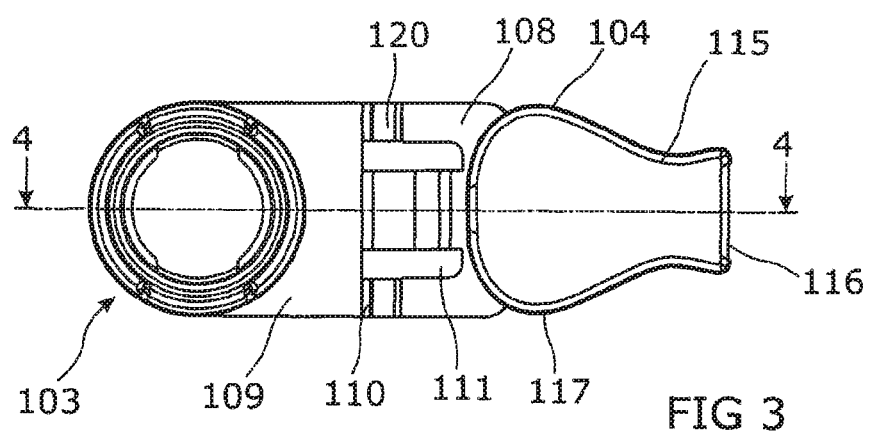

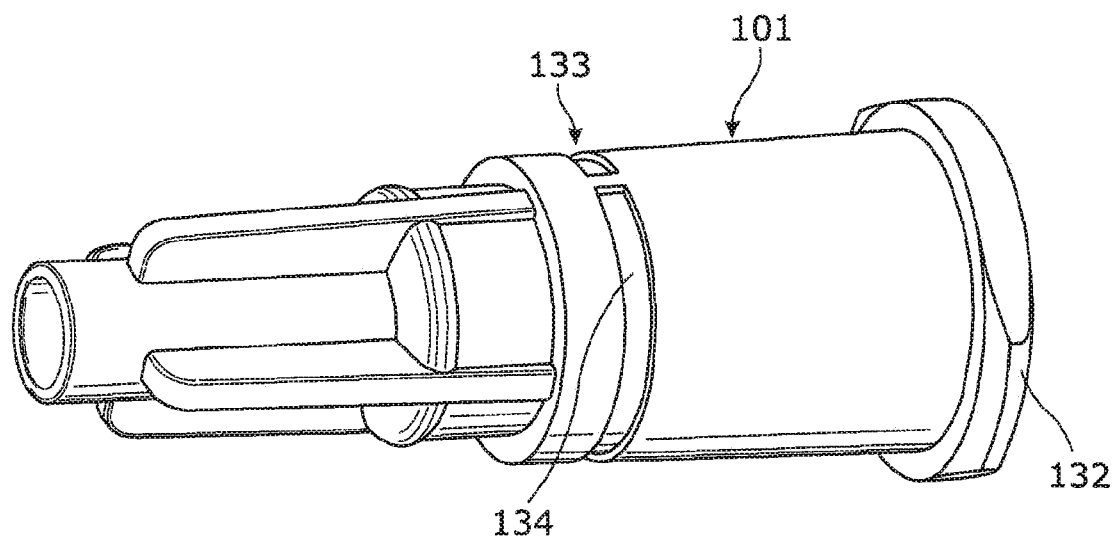
FIG 15
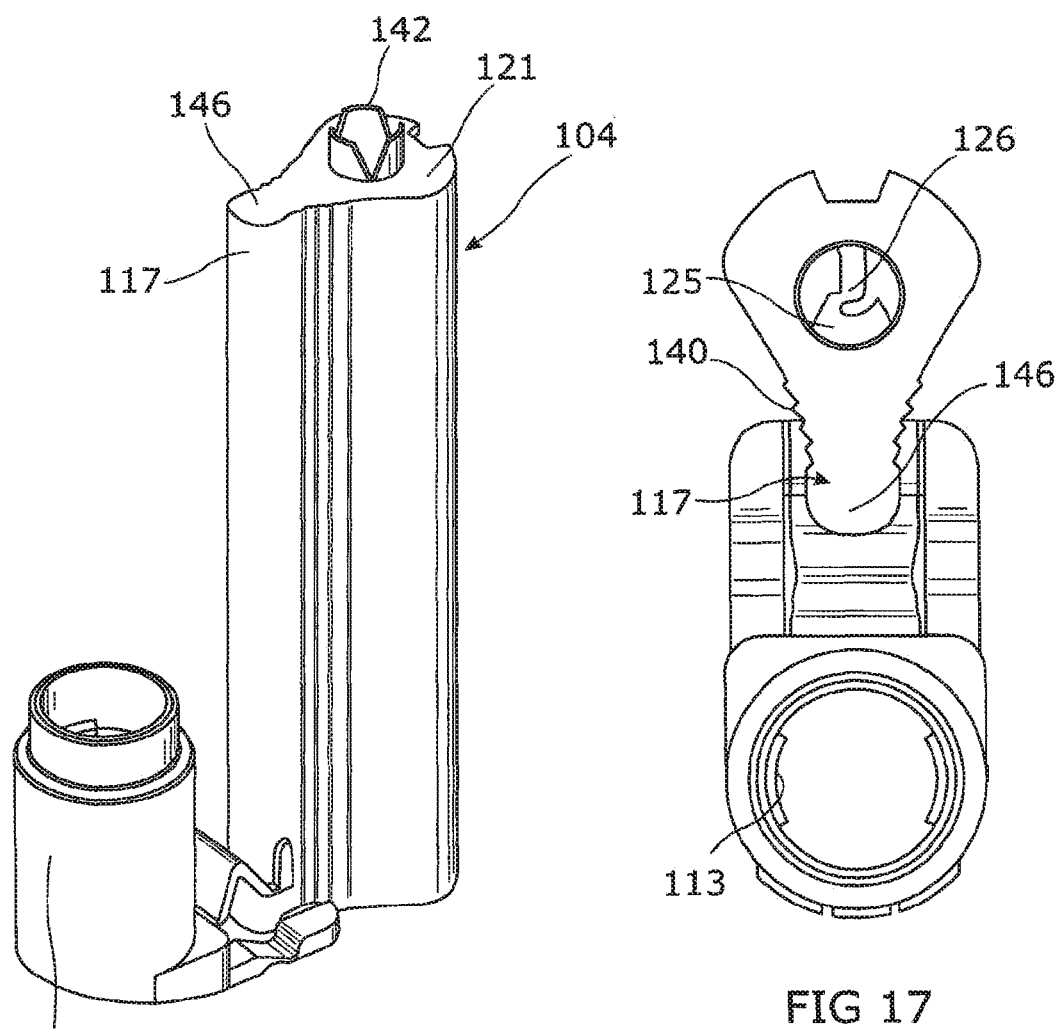
FIG 16
FIG 17

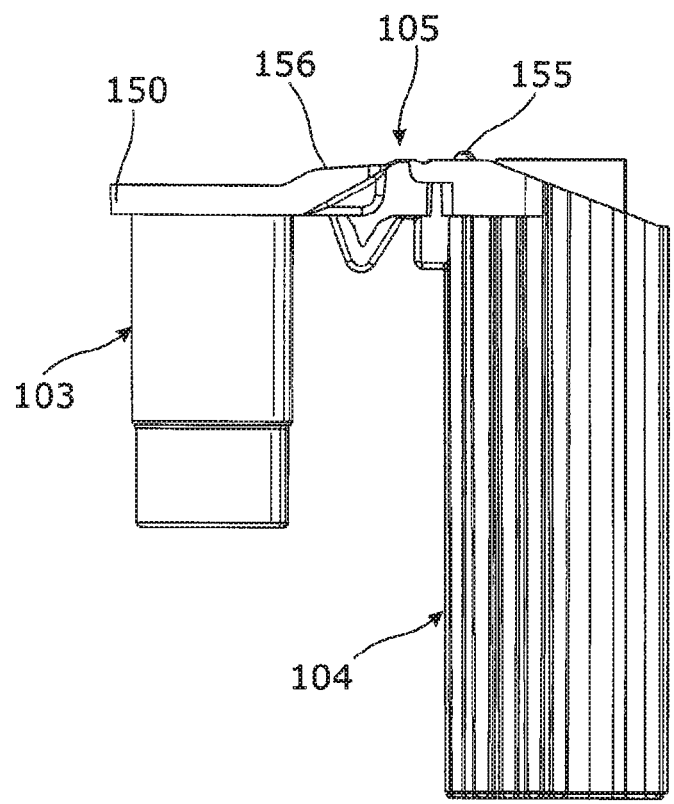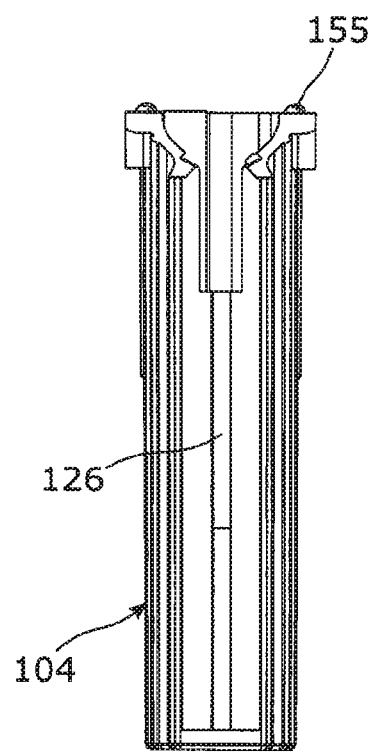
FIG 20　　　　　FIG 21
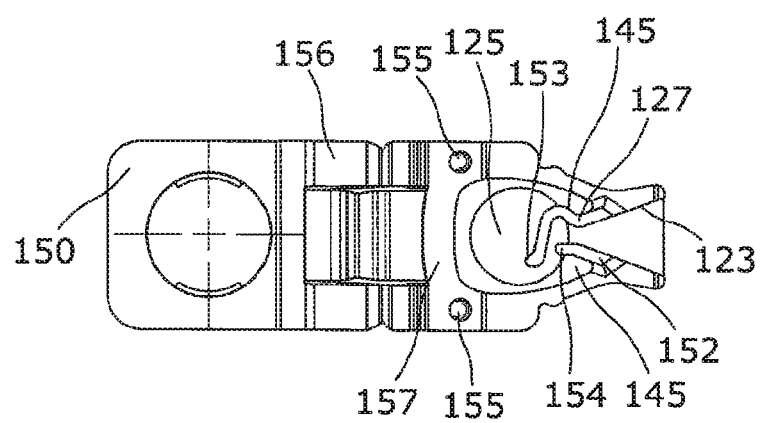
FIG 22

NEEDLESTICK PREVENTION DEVICE

This invention relates to a needlestick prevention device for use with injection devices such as syringes.

A needlestick injury generally occurs in a medical environment, and particularly during use of a syringe or other injection device, when the user accidentally sticks the needle into himself or herself, or indeed another person. Such needlestick injuries are a major cause of spreading infections and disease, and are painful and possibly incapacitating, so it is important to prevent them.

There are various known ways of trying to prevent needlestick injuries. An injection needle is commonly supplied with a protective cap, which is removed for use, and is then disposed of, as it is not recommended that the cap is replaced over the needle. Indeed, it is thought that replacement of the cap has been the cause of a significant number of needlestick injuries.

The needle itself may be mounted on a cylindrical collar at the distal end of a syringe barrel. Alternatively, it may be mounted on a separate hub, which is then attached to the syringe barrel. The connection between the hub and the syringe barrel is typically by means of a luer connection, comprising a conical male portion on the barrel and a complementary female portion on the hub. The conical taper is a standard 6°. The connection may be a luer slip type, which is a simple friction fit, or a luer lock type, where the male portion is surrounded by an internally threaded collar, and the hub has external radial lugs to engage in the screw thread. The hub is then, in effect, screwed onto the collar. A further alternative is for the radial lugs to engage behind an undercut on the collar at the distal end of the syringe. The hub is then a push fit on the syringe, being retained by the lugs behind the undercut.

One way of preventing needlestick injuries is to provide a safety shield, mounted on the needle-bearing member, that is, the syringe or the hub, to provide protection for the needle once the disposable cap is removed. The shield pivots away from the needle for use, and is then pivoted back and locked in a position where the needle is shielded. Such an arrangement adds to the complexity and cost of the item, as it requires an extra part.

Another proposal is to mould a safety shield in one piece with the needle and hub. A protective strip ensures the needle is not exposed before use, the strip being removed for use. Again, the shield pivots away from the needle for use, and is pivoted back and locked in a position where the needle is shielded. This arrangement may be difficult to mould, and is not suitable for syringes having an integrated needle.

It has also been proposed to replace the disposable cap with a safety shield. In this case it is of course essential that the safety shield is not removable in the same way as the disposable cap. It is relatively easy to provide a connection between the injection device and the safety shield which prevents removal but this may result in the shield not being orientable on the device. This has the disadvantage that the user normally requires the needle to be in a "bevel up" orientation for injection, but without the shield being a hindrance. If the shield is not rotatable on the device the orientation of the shield and needle cannot be guaranteed, and if it is freely rotatable it may naturally rotate to a position in which it is in the way.

The majority of needlestick injuries are caused after injection has taken place. Typically, the injection device is filled by the user and the injection given immediately. Increasingly however, injections are made up of several different medications, and the injection device is then filled in one location, such as a pharmacy, and then transported to the recipient for injection. To remove the risk of needlestick injury, this requires the needle to be covered again in a transport position, but not to be locked, so that it can be uncovered for injection. It is important that the transport position is clearly distinguishable from the locked position, and that the safety shield cannot move accidentally into the use position or the locked position during transport.

WO2017/129968, which also claims priority from GB1621266.4, shows a needlestick prevention device comprising a safety shield which replaces a disposable cap. The device is mounted on a needle-bearing member and the movable shield has transport, use and locked positions. The transport position is provided by a transport recess and the locked position by a locking recess, the recesses being connected by a gate device at least at the base of the needle, to prevent movement of the needle out of the locking recess once it has entered it. The shield is moved from the use position to the transport position by a living hinge, a further manual force being needed to move it into the locked position. It has been found that when the shield returns to the transport position following injection, the energy provided by the living hinge causes the shield to strike the base of the needle, resulting in vibration of the needle. If there is any blood on the tip of the needle, the vibration can flick this off, causing it to splatter and it may spray out of the device, resulting in a hazard for the user.

According to a first aspect of the invention, a needlestick prevention device for an injection needle carried by a needle-bearing member of a syringe is formed as a one-piece moulding and comprises a first part adapted to be attached to the needle-bearing member and a second part providing a shield for the needle and pivotally movable relative to the first part to expose the needle for use, the device being adapted to adopt a first position in which the needle is protected for transport of the device prior to use, a second position in which the needle is exposed for filling of the syringe and injection, a third position in which the needle is protected after filling of the syringe but before injection and a fourth position in which the needle is locked in the device following injection, the shield having a transport recess and a locking recess connected by a gate device, the arrangement being such that in the third position the needle is in the transport recess and is able to move into the second position, and in the fourth position the needle moves through the gate device into the locking recess, with the gate device preventing movement out of the fourth position.

This arrangement provides a clearly defined transport position, and a simple and safe construction for the fourth position in which the needle is locked. The locking recess contains the needle securely, and is retained by engagement with the gate device, so it is virtually impossible to remove the needle from the locking recess without significant damage. This provides the desired protection against needlestick injuries.

Conveniently, the device including energy-dissipating means operative to reduce the energy of the second part as it is returned to the third position and before the gate device contacts the needle.

The energy-dissipating means reduces the energy of the second part as it returns to the third or transport position, before the gate device contacts the needle, so that the tendency to cause vibration of the needle and spray or splatter any liquid on the tip of the needle is significantly reduced.

The first and second parts of the device are preferably connected by a living hinge. The hinge provides the force to move the second part between the first and second positions, and between the second and third positions, once movement is initiated by the user. Further manual force is required to move the second part into the fourth position. The hinge also retains the second part in the first and third positions. The energy-dissipating means is only operative at the end of the travel of the second part into the third position, so that it does not affect the ability of the hinge to move the second part into the third position. This provides a particularly simple construction, as no further means are required to retain the second part in the various positions.

Conveniently the first and third positions are the same, so that the second part is initially in the transport recess. The second part is then movable between the second and third positions as required.

Conveniently the energy-dissipating means comprises one or more bumps provided on one of the first and second parts, and adapted to contact a corresponding surface on the other of the first and second parts before the gate device contacts the needle. This provides a simple and effective construction for the energy-dissipating means.

Preferably a pair of bumps is provided. Conveniently the bumps are provided on the second part, adjacent the hinge.

The gate device may be provided along part or the whole length of the needle. In one embodiment the gate device is provided at least at the base of the needle. This provides a particularly secure locking of the needle in the locking recess. In a preferred embodiment the gate device is provided for a central portion of the needle. This means that the travel of the second part is increased before the gate device contacts the needle in comparison with a construction where the gate device is provided at the base of the needle. The gate device preferably includes a projection formed in the second part to define a partition between the transport recess and a locking recess and a curved or labyrinthine path connecting the transport recess and the locking recess. When the needle is moved into the third position from the second position, it is retained in the transport recess by the projection, but can follow the labyrinthine path into the locking recess when the further manual force is applied. The labyrinthine path is arranged so that once in the locking recess, the needle cannot return along the labyrinthine path round the projection.

The second part preferably has an extension leading from the transport recess in a direction away from the locking recess to shield the needle when it is in the first and third positions. The extension may be a funnel to guide the needle into the transport recess.

The labyrinthine path is conveniently defined by two opposing projections. These may extend from respective sides of the funnel. A first projection curves across the centre line of the second part to form a stop for the third position, and its free end is recurved. A second projection extends towards the locking recess and its free end is angled outwardly.

The locking recess may be formed in an enlarged portion of the second part. This may be easily grasped by the user to initiate movement between the first and second and second and third positions. It may also be grasped or used to apply the manual force to move the second part into the locked position. Alternatively, a finger plate may be provided on the second part and used to apply the manual force. The second part may then not require the enlarged portion.

In a preferred embodiment the first and second parts are able to adopt three stable positions, where the first and third positions are the same. In the first position the needle is accommodated in the transport recess in the second part, and the hinge maintains the relative positions of the first and second parts. This is the initial position, in which the device is assembled with the needle-bearing member, and in which it can be transported prior to use. If the needle-bearing member is a hub, the hub and device are attached to the syringe with the device in this initial position. In the second position the second part is pivoted away from the first part to expose the needle. This is the operative position, in which a syringe can be filled and an injection given. If the injection is not to be given immediately, the second part can be moved back into the first position, and maintained there by the hinge with the needle covered. In this position the syringe can be carried safely if necessary, so that it is in the transport position. Then the second part can be moved into the operative position again when the injection is to be given. Following injection, the device is placed in the fourth position, in which the second part is moved back, through the first position and the gate device into the locking recess for permanent locking. This is the locked position, in which the needle is once more shielded to prevent needlestick injuries.

The first part may be attached to the needle-bearing member by attachment means providing for the rotation of the needlestick prevention device relative to the needle-bearing member but preventing removal of the device. Conveniently, the attachment means comprises a projection on one of the needle-bearing member and the needlestick prevention device, and a groove on the other. Preferably, the projection is provided on the needlestick prevention device, and the groove on the needle-bearing member. The needlestick prevention device may be rotatable through 360° relative to the needle-bearing member. Alternatively the rotation may be limited, so that the needlestick prevention device is rotatable relative to the needle-bearing member through an angle between about 100° and substantially 180° in each direction. In such an embodiment the groove conveniently extends round the two separate arcs of the circumference of the needle-bearing member, the adjacent ends of the arcs being separated by any desired distance. The needlestick prevention device is formed with a pair of projections, diametrically opposed, with each projection accommodated in a respective arc of the groove. In a further embodiment the groove may be provided round part of the circumference of the needle-bearing member, and one or two projections arranged on the device to provide the required angle of rotation. Preferably two projections are provided, to aid stability of rotation while minimising the material used.

According to a second aspect of the invention, a needlestick prevention device for an injection needle carried by a needle-bearing member of a syringe is formed as a one-piece moulding and comprises a first part adapted to be attached to the needle-bearing member and second part providing a shield for the needle and pivotally movable relative to the first part to expose the needle for use, the first part being attached to the needle-bearing member by attachment means providing for the rotation of the needlestick prevention device relative to the needle-bearing member through an angle between about 100° and substantially 180° in each direction, but preventing removal of the device, the attachment means comprising a groove on the needle-bearing member, and a projection on the needlestick prevention device, with the groove extending round two separate arcs of the circumference of the needle-bearing member, the adjacent ends of the arcs being separated by any desired distance, and the needlestick prevention device being formed with a pair of projections, diametrically opposed, with each projection accommodated in a respective arc of the groove.

This arrangement ensures that the device cannot be removed from the needle-bearing member but can be oriented such that it is not in the way of an injection being given, with the needle in the bevel up position.

Preferably the first part is not freely rotatable on the needle-bearing member. Instead the engagement between them is arranged to allow rotation when a torque is applied manually, and for the members to remain in their relative position when the torque is removed. This arrangement may be provided by a frictional engagement between the first part and the needle-bearing member.

An embodiment of a needlestick prevention device according to the aspects of the invention is illustrated, by way of example only, in the accompanying drawings, in which:—

FIG. 1 is perspective view of a needlestick prevention device according to the invention;

FIG. 3 is an end view of the device of FIG. 1;

FIG. 15 is a perspective view of a needle hub;

FIG. 16 is similar to FIG. 12 but shows a further modification; and

FIG. 17 is an end view of the device of FIG. 1;

FIG. 20 is a side view of the device of FIG. 18;

FIG. 21 is an end view of the device of FIG. 18;

FIG. 22 is a top view of the device of FIG. 18; and

Figure 2:
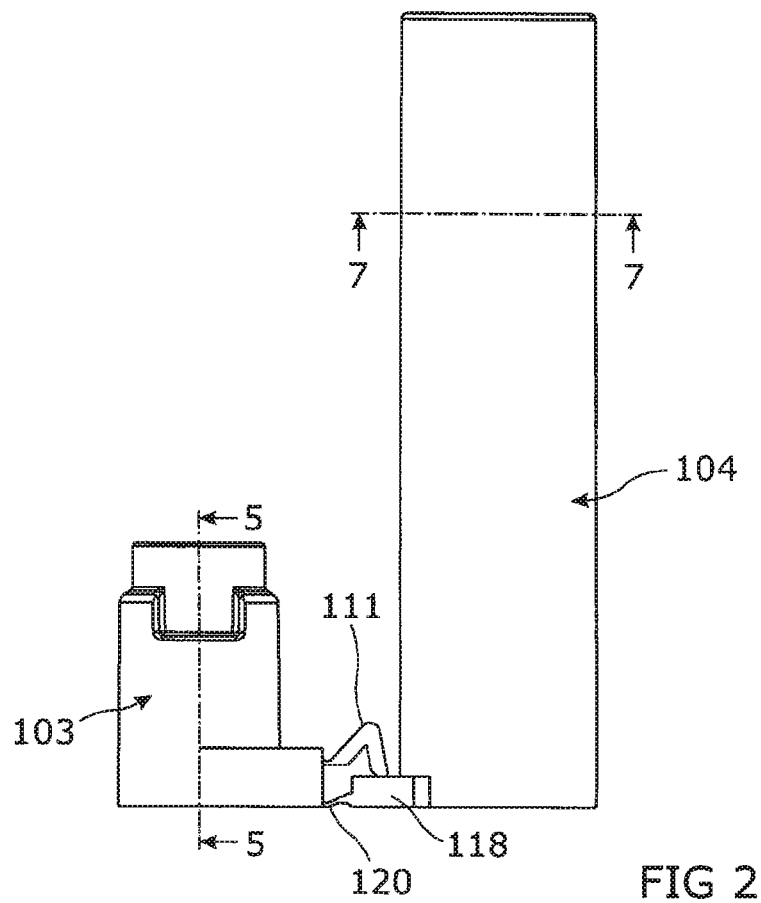
FIG. 2 is a side view of the device of FIG. 1.
Figure 7:
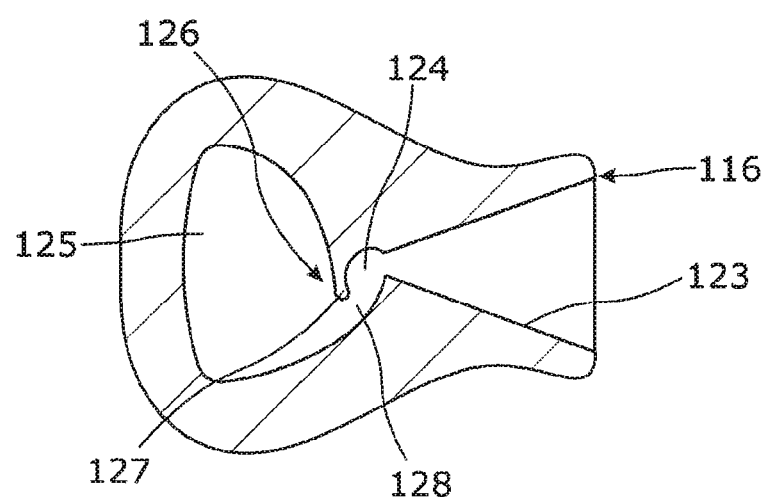
FIG. 7 is cross-section along the line 7-7 of FIG. 2.
Figure 4:
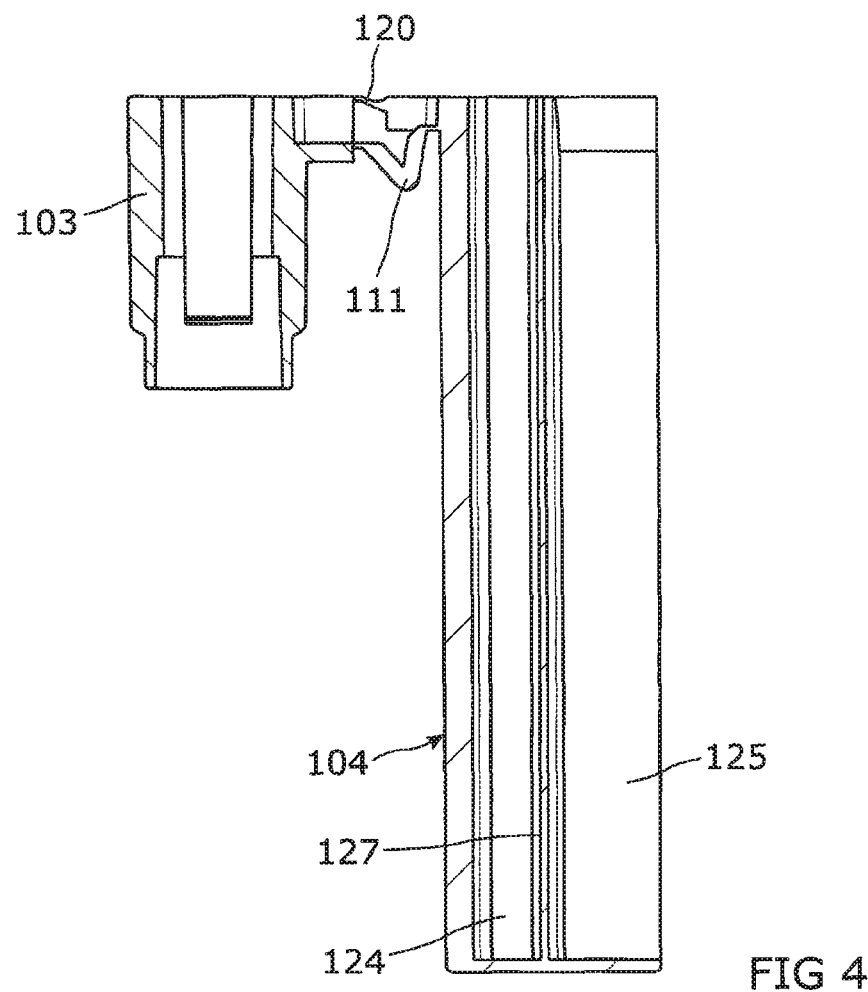
FIG. 4 is a cross-section along the line 4-4 of FIG. 3.

FIGS. 1 to 7 show a needlestick prevention device 100 for an injection needle carried by a needle-bearing member such as a syringe barrel or a needle hub. FIGS. 8 to 11 show the device 100 attached to a needle hub 101 and a syringe 102. The device 100 is intended to replace the standard disposable cap which is typically provided to shield the needle before use, and to provide a safety device which can be used on standard syringes and hubs, as well as being easy and inexpensive to make and assemble.

The device 100 is made as a one-piece moulding of a plastics such as polypropylene. It comprises a first part 103 adapted to be attached to a needle-bearing member (not shown in FIGS. 1 to 7) and a second part 104 providing a shield for the needle, and pivotally movable relative to the first part 103 to expose the needle for use.

Figure 10:
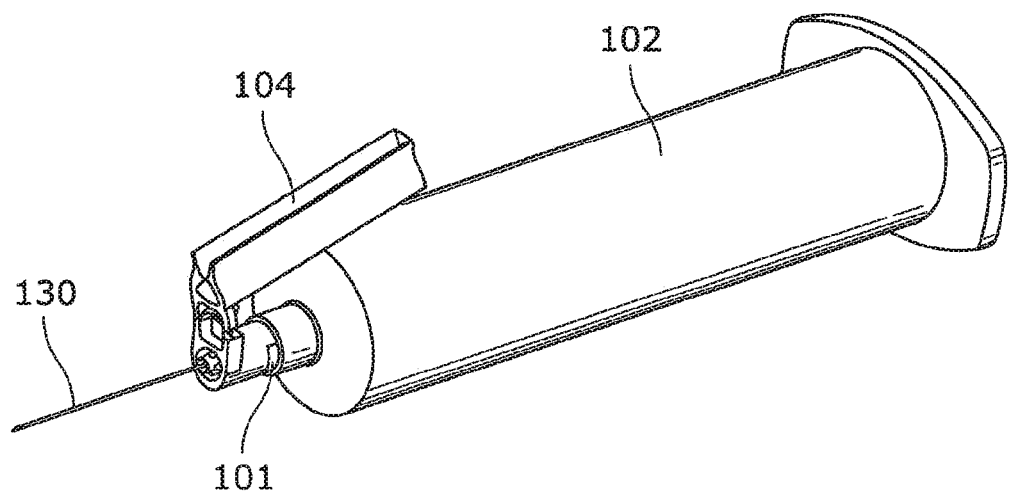
FIG. 10 shows the device in the operative position on a syringe barrel.
Figure 11:
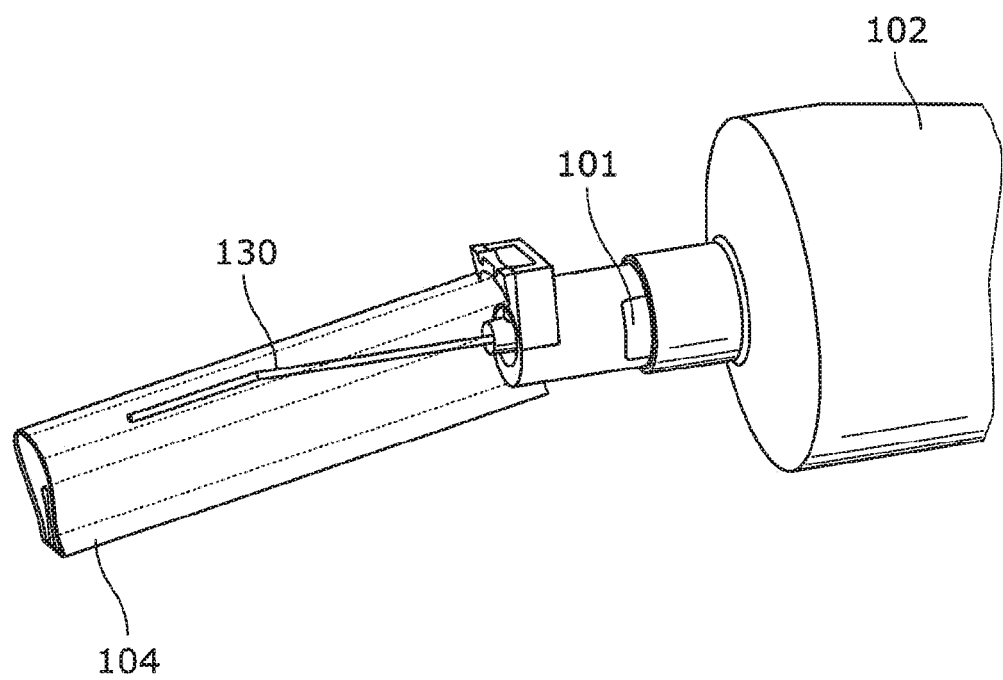
FIG. 11 is similar to FIG. 10 but shows the device in the locked position.

The first and second parts 103, 104 are connected by a hinge 105. This allows the first and second parts 103, 104 to adopt three stable positions. The first position is an initial position and a transport position, and can be seen in FIG. 9. The second position, shown in FIGS. 1 and 2, as well as FIG. 10, is an open or operative position, in which the needle is exposed for use. The third position, shown in FIG. 11, is a locking position, in which the two parts 103, 104 are held firmly, and the needle is trapped in the second part 104.

The first part 103 comprises a cylindrical portion 106 having a free end 107 adapted to be connected to the needle-bearing member 101 or 102. The other axial end 108 has a pair of arms 109 projecting laterally. The outer end 110 of each arm 109 is attached to the second part 104 to form two hinge points, and the arms 109 also carry one end of a hinge spring 111.

Figure 5:
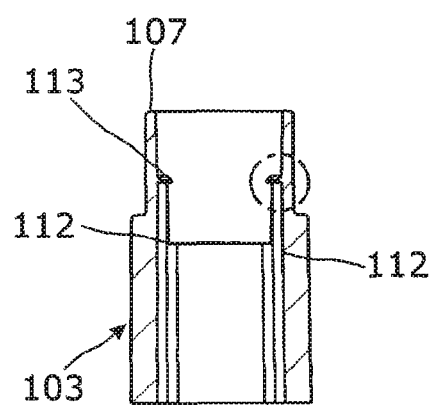
FIG. 5 is a cross-section along the line 5-5 of FIG. 2.
Figure 6:
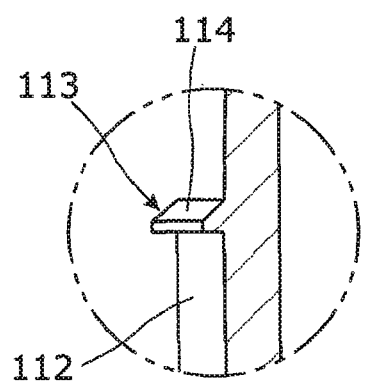
FIG. 6 is a detail of part of FIG. 5.

The free end 107 terminates in a smaller diameter portion 129 which can be received in a standard attachment of a syringe. The first part 103 has a pair of diametrally opposed axial ribs 112 extending from the end 108 and terminating short of the free end 107. As best seen in FIGS. 5 and 6, each rib 112 has an internal projection 113, which is used to attach the device 100 to a needle-bearing member, as explained in more detail below with reference to FIG. 8. Each projection 113 has a substantially triangular profile, having a face inclined to the axis, and an abutment face 114 perpendicular to the axis.

The second part 104 is a substantially U-shaped shield member. As best seen in FIG. 3, the outline is indented at 115 adjacent the open side 116 and the closed part 117 is slightly bulbous. This makes it easy for the user to grasp the second part 104.

At the end of the second part 104 adjacent the first part 103 a pair of arms 118 project laterally, and attach to the respective arms 109 on the first part at the hinge points 120. The arms 118 carry the other end of the hinge spring 111. The free end 121 of the second part 104 is closed at 122.

The open side 116 allows for passage of the needle between the initial position and the open position, and between the open position and the transport position. The open side 116 is formed with a funnel 123 leading to a transport recess 124 which in turn leads to a locking recess 125 through a gate device 126. The transport recess 124 extends along the axis of the device 100 so that it accommodates the needle in the initial and transport positions. The gate device 126 comprises a projection 127 defining a position between the recesses 124 and 125 and a curved or labyrinthine path 128 between them. The projection extends all the way along the axial length of the second part 104, but could be provided only at the end adjacent the first part 103, that is, adjacent the base of the needle.

The device 100 can be manufactured simply by injection moulding.

Figure 8:
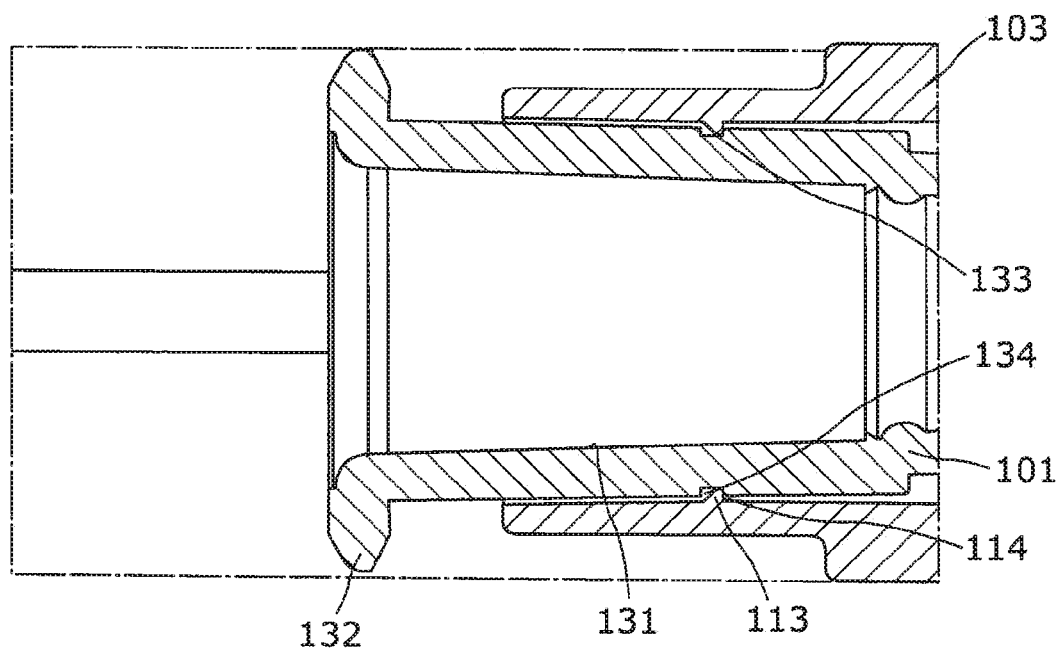
FIG. 8 is a sectional view of the connection between the device of FIG. 1 and a needle hub.

Once manufactured, the device 100 is assembled to a needle-bearing member such as the needle hub 101 shown in FIG. 8. The hub 101 is also typically of polypropylene, and is manufactured by injection moulding.

The needle 130 may be moulded with the hub 101, or assembled afterwards. The hub 101 is of a standard construction, with a conical bore 131 for attachment to a syringe 102, and an out-turned flange 132 at its proximal end. Because the device 100 is replacing the standard disposable cap, it is important that it cannot be removed in the same way as a standard cap. The hub 101 is therefore formed with an external groove 133 made of two arcuate parts 134 extending through about 100°, so that their adjacent ends are separated by an arcuate distance of about 80°. The hub 101 is assembled with the device 100 by introducing the hub 101 into the free end of the first part 103 until the projections 113 each engage in a respective groove part 134. The projections 113 slide along their inclined faces into the groove parts 134, but the abutment faces 114 engage with the groove parts 134 to resist separation of the device 100 and hub 101. However, the device 100 is able to rotate through about 100° in each direction on the hub 101. The engagement between the first part 103 and the hub 101 has sufficient friction to allow the first part 103 to rotate relative to the hub 101 when a torque is applied manually by the user, but to remain in position when the torque is removed. When the device 100 and the hub 101 are assembled the needle 130 will be accommodated in the transport recess 124, and the device 100 will be maintained in the initial position by the hinge 105.

Figure 9:
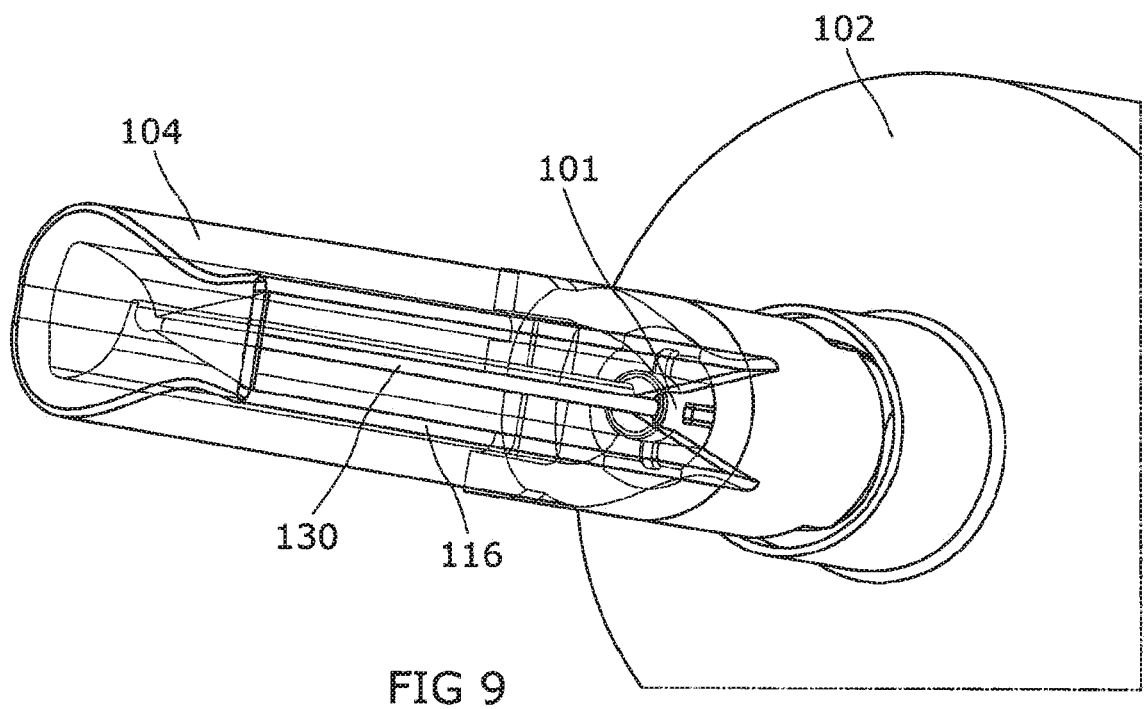
FIG. 9 is a perspective view of the device of FIG. 1 mounted on a syringe barrel.

For use, the assembled device 100 and hub 101 are removed from any packaging and attached to a syringe 102, as shown in FIG. 9. The user then moves the second part 104 into the open position of FIG. 10, by grasping the bulbous part 117 and applying a manual force in a direction such that the needle 130 starts coming out of the open side 116. The hinge 105 then operates to move the second part 104 pivotally to the open position. The user can then fill the syringe 102 in the usual way.

The injection may be given immediately. However, if this is not possible, the needle 130 may again be shielded by moving the second part 104 back to the transport position. Once again the user needs only to apply a small manual force to start the movement, as the hinge 105 will continue the movement until the needle 130 is in the transport recess 124. There is no risk of a needlestick injury if the syringe is carried by the user as the hinge 105 retains the second part 104 in this stable transport position. When the injection is to be given the second part 104 is again moved into the open position.

Because the device 100 can be rotated in each direction through about 100° on the hub 101, the second part 104 can always be moved out of the user's way when the needle 130 is in the preferred bevel up orientation for injection, and can be maintained in a stable position by the frictional engagement between the first part 103 and the hub 101.

After injection the user again moves the second part 104 back towards the first part 103, with the hinge 105 operative to ensure it reaches the transport position. The user then applies a further force in the same direction to move the needle 130 through the gate device 126 and into the locking recess 125. It will be appreciated that the needle 130 moves round the projection 127 along the path 128 into the locking recess 125. The locked position is shown in FIG. 11. The needle 130 is held securely, particularly by the base of the needle 130, which does not have the flexibility to return along the path 128. It will also be noted that the free end of the needle 130 is distorted by its engagement with the back of the locking recess 125, thus rendering it useless. The syringe 102 can be disposed of safely.

As the needle 10 moves into the transport position it is guided by the funnel 123. If the needle is distorted during injection, for example by hitting a bone accidentally, the funnel 123 will guide it back and may even remove at least some of the distortion, ensuring that it can enter the locking recess 125.

In a modification (not shown), the closed part 117 of the second part 104 may not be as bulbous. A finger plate may be provided on the second part 104, for example opposite the open side 116, for grasping by the user in moving the second part 104 to the open position. In a further modification (not shown), the gate device 126 may be modified by changing the profile of the projection 127 adjacent the base of the needle to ensure that the needle cannot return from the locked position.

Figure 12:
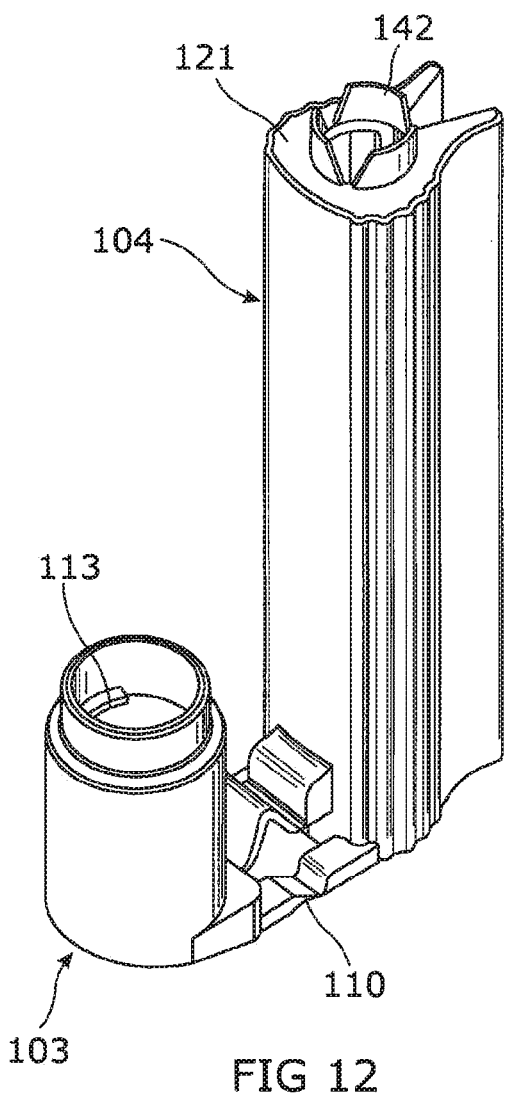
FIG. 12 is similar to FIG. 1 but shows a modification.
Figure 13:
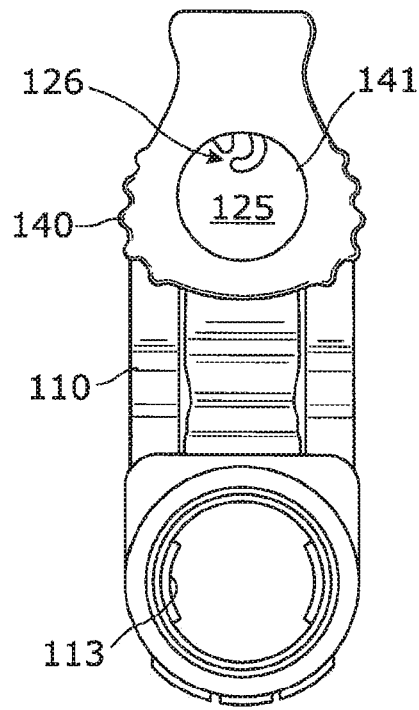
FIG. 13 is an end view of the device of FIG. 12.
Figure 14:
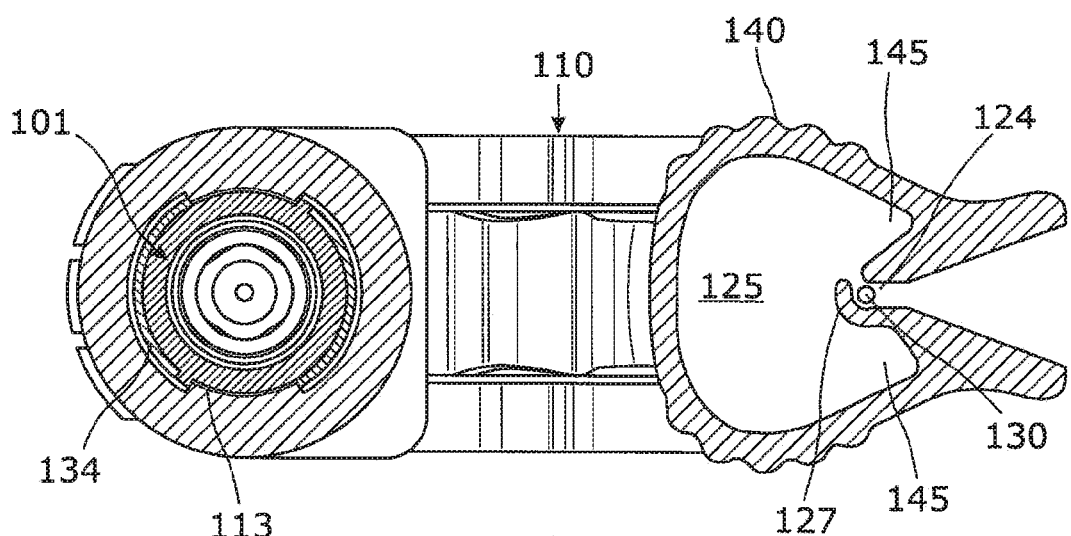
FIG. 14 is a section through a needle hub and the device of FIG. 12, showing the connection between them.
Figure 18:
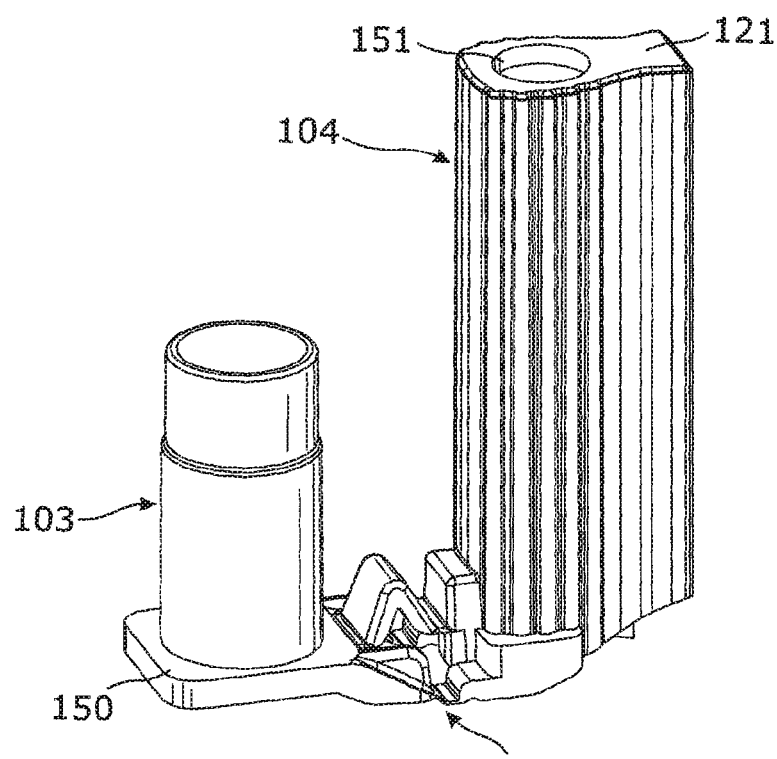
FIG. 18 is similar to FIG. 12 and shows yet a further modification.
Figure 19:
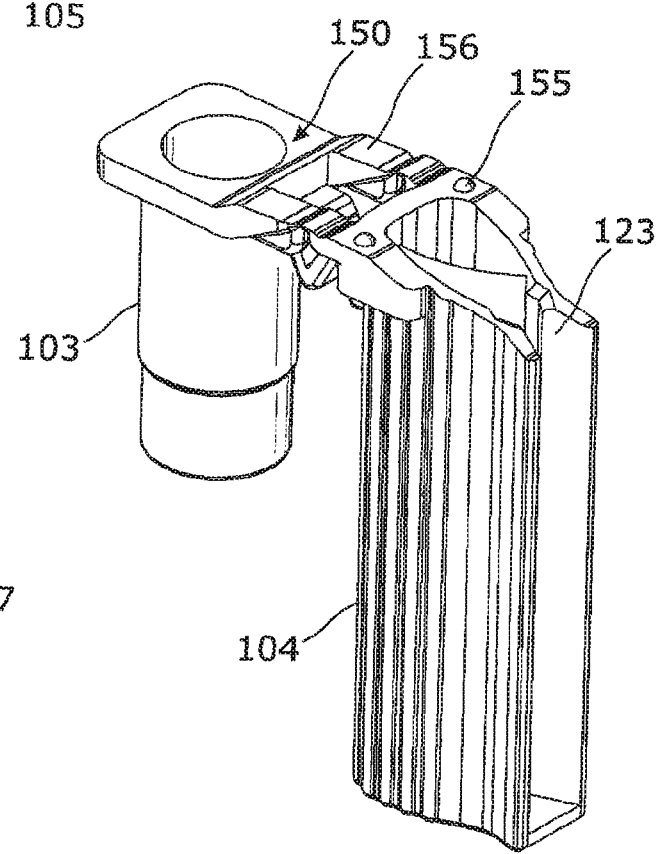
FIG. 19 is a perspective view of the device of FIG. 18 from the opposite side.

FIGS. 12 to 14 show a modification of the device of FIGS. 1 to 11, and corresponding reference numerals have been applied to corresponding parts. FIGS. 12 to 14 show the second part 104 as a similar external shape with a bulbous closed part 117, which also has external axial ribs 140 for ease of grasping by the user. FIG. 12 also shows how the closed end 122 of the second part is formed. The second part 104 has a central aperture 141 surrounded by three flaps 142, whose dimensions are chosen so that in the same plane as the end 122 they will close the central aperture 141. When the device is removed from the mould the flaps 142 will be upstanding as shown, and will be sealed to complete the end 122 as a post-moulding step.

FIGS. 12 to 14 also show a modification of the gate device 126. It still forms a barrier between the transport and locking recesses 124 and 125, but the sharp corner shown in FIG. 7 has been smoothed, so that the path of the needle is eased. The position of the needle in the transport recess (the first and third positions) is also shown. The locking recess 125 is modified with extensions 145 towards the transport recess 124 on each side of the gate device 126. This provides enhanced security, as if the needle in the locked position enters one of these extensions it is much more difficult, if not impossible, for it to return through the gate device 126.

FIGS. 14 and 15 also show the connection of the device 100 and the hub 101. FIG. 15 shows the form of the groove 133. In FIG. 15 there is a relatively small distance between the adjacent ends of the groove parts 134, but the radial depth of the groove is increased. FIGS. 12 to 14 also show a modification of each projection 113. The projections 113 have a greater circumferential extent and also a greater radial depth. The separation distance between the adjacent ends of the groove parts 134 and the circumferential extent of the projections 113 are chosen to ensure that the device 100 can rotate a sufficient distance to be out of the way when the syringe is being filled and when the injection is given. The rotation should be at least 90°, and will clearly be less than 180°. The amount is preferably about 115°, but could be anywhere in the range—for example, 100°, 110°, 120°, 130°. This modification provides a more secure attachment. In particular, it ensures that the connection will remain secure when the hub 101 is attached to a syringe by a luer lock connection. Otherwise the construction and operation of the embodiments of FIGS. 12 to 15 is the same as that of FIGS. 1 to 11.

It may be preferable for the device 100 to be rotatable through a greater angle, but still less than 360°. In a modification (not shown), a single groove 133 may be provided, extending for a greater circumferential angle, and one or two projections arranged to provide the required angle of rotation. Preferably two projections are provided, to aid stability of rotation while minimising the material used.

FIGS. 16 and 17 show a further modification of the closed part 117 of the second part 104. Otherwise this embodiment is the same as that of FIGS. 12 to 15, and corresponding reference numerals have been applied to corresponding parts. In FIGS. 16 and 17, instead of being bulbous the closed part 117 of the second part 104 is provided with an extension 146 of reduced width. The extension 146 also has axial ribs 140. While the enlarged portion of FIGS. 1 to 15 is easy to grasp for the user, the reduced width extension of FIGS. 16 and 17 may be preferred in some circumstances. In a further modification (not shown) a finger plate may be provided on the second part 104, for example opposite the open side 116, for grasping by the user in moving the second part 104 to the open position. It would also be possible to provide an axial nib at the free end 121, if preferred. In a further modification (not shown), the gate device 126 may be modified by changing the profile of the projection 127 adjacent the base of the needle to ensure that the needle cannot return from the locked position.

FIGS. 18 to 23 show another modification of the device of FIGS. 12 to 15, and corresponding reference numerals have been applied to corresponding parts. These show a modification of the gate device 126 and the labyrinthine path 128 and energy-dissipating means in the form of bumps provided on the second part 104.

In FIGS. 18 to 23 the first part 103 is similar to the device of FIGS. 12 to 14, although the cylindrical part is now mounted on an enlarged flange 150 to which the hinge 105 is attached. The second part 104 has an aperture 151 at the end 121, rather than being closed, for ease of moulding.

FIG. 21 shows that the length of the gate device 126 is reduced, so that it extends approximately along the central third of the axial length of the second part 104. The configuration of the gate device is also changed. It is defined by two opposing projections 127 and 152, extending respectively from each side of the inner end of the funnel 123 towards the locking recess 125. The projection 127 is longer in comparison with that of FIG. 12, and curves first outwardly and then inwardly and across the centre line of the part 104 to form a stop for the transport position. Its free end 153 is recurved. The projection 127 in this embodiment is more flexible and resilient than that of FIG. 12. The projection 152 extends in the direction of the funnel side and at its free end 154 is angled outwardly, and spaced from the projection 127. The labyrinthine path 128 is therefore lengthened, such that the needle 130 moves further sideways or outwardly before reaching the free end of projection 127 to enter the locking recess 125. The recurved free end 153 of the projection 127 assists the entry of the needle into the locking recess 125. The projection 127 also flexes resiliently as the needle travels along the path 128 to assist entry of the needle into the locking recess 125, and then returns to its original position. It is therefore extremely difficult for the needle 130 to return from the locking recess 125 to the transport position. It will be appreciated that the extensions 145 of the locking recess 125 are even deeper in this embodiment, and that the recurved free end 153 also serves to deflect the needle 130 away from the entry to the labyrinthine path 128 from the locking recess 125. The alteration to the labyrinthine path 128 to make it more difficult for the needle 130 to return from the locking recess 125 is necessitated in part by the change in length and position of the gate device 126.

The embodiments of FIGS. 1 to 17 were found to have a problem with splatter. When the second part 104 was moved back to the transport position after performing an injection, the energy of the part 104 imparted by the hinge caused the gate device 126 to strike the base of the needle 130, resulting in vibration of the needle 130. Any blood on the end of the needle 130 was flicked off in a splatter pattern, and could spray out of the device. This posed a danger to the person using the device.

Figure 23:
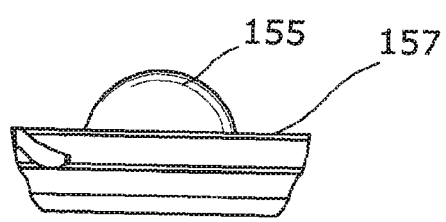
FIG. 23 is a detail of part of FIG. 20.

The embodiment of FIGS. 18 to 23 has features that overcome this problem. The first is the position of the gate device 126. Shortening it and moving it away from the base of the needle 130 means that it strikes the needle later. The second feature is the provision of means to dissipate the energy of the second part 104 in the final portion of its travel, but without reducing the closing force such that the needle does not return to the transport position. As best seen in FIGS. 22 and 23, the energy dissipating means comprises a pair of small hemispherical bumps 155 formed on the part 104 adjacent the hinge 105. The bumps 155 are spaced apart. As the part 104 moves into the transport position from the open position, the bumps 155 contact the corresponding surface 156 on the flange 150 of the first part 103 before the larger surface 157 of the second part 104 makes contact. This dissipates the energy of the second part 104 without affecting the closing force. The timing is such that the energy is dissipated before the gate device 126 strikes the needle 130, so that vibration of the needle 130 and thus splatter, is substantially prevented.

Otherwise, the operation and use of the embodiment of FIGS. 18 to 23 is the same as that of FIGS. 12 to 14.

The embodiments described provide a simple construction of needlestick prevention device which is simple to make and to use, while ensuring safe transport.

The invention claimed is:

1. A needlestick prevention device for an injection needle carried by a needle-bearing member of a syringe,
in which the device is formed as a one-piece moulding and comprises a first part adapted to be attached to the needle-bearing member and a second part providing a shield for the needle and pivotally movable relative to the first part to expose the needle for use, wherein the second part defines a center line, the device being adapted to adopt a first position in which the needle is protected for transport of the device prior to use, a second position in which the needle is exposed for filling of the syringe and injection, a third position in which the needle is protected after filling of the syringe but before injection and a fourth position in which the needle is locked in the device following injection, the shield having a transport recess and a locking recess connected by a gate device, the arrangement being such that in the third position the needle is in the transport recess and is able to move into the second position, and in the fourth position the needle moves through the gate device into the locking recess, with the gate device preventing movement out of the fourth position, wherein the gate device includes two opposing projections formed in the second part to define a partition between the transport recess and a locking recess and a curved path from the transport recess to the locking recess, the two opposing projections comprising a first projection, and a second projection, wherein the first projection includes a first portion that extends away from the center line and a second end portion that extends from the first portion toward and across the center line to define a distal end of the first projection, and wherein the second projection extends towards the locking recess with a free end of the second projection angled outwardly and spaced from the first projection; and wherein the first and second parts of the device are connected by a living hinge which provides a force to move the second part between the first and second positions once a first movement is initiated by the user, and wherein the living hinge provides a force to move the second part between the second and third positions but not into the fourth position once a second movement is initiated by the user.

2. A needlestick prevention device as claimed in claim 1, in which the device includes energy dissipating elements operative to reduce the energy of the second part as it is returned to the third position and before the gate device contacts the needle.

3. A needlestick prevention device as claimed in claim 1, in which the hinge also retains the second part in the first and third positions.

4. A needlestick prevention device as claimed in claim 1, in which the first and third positions are the same, so that the second part is initially in the transport recess.

5. A needlestick prevention device as claimed in claim 2, in which the energy dissipating elements comprises one or more bumps provided on a surface of one of the first and second parts, and adapted to contact a corresponding surface on the other of the first and second parts to reduce the energy of the second part as it is returned to the third position and before the gate device contacts the needle, one of the surface and the corresponding surface being provided on a flange to which the hinge is attached.

6. A needlestick prevention device as claimed in claim 5, in which the one or more bumps includes two bumps.

7. A needlestick prevention device as claimed in claim 5, in which the bumps are provided on the second part, adjacent the hinge.

8. A needlestick prevention device as claimed in claim 1, in which the gate device is provided along part or the whole length of the needle.

9. A needlestick prevention device as claimed in claim 1, in which the gate device is provided at least at a base of the needle.

10. A needlestick prevention device as claimed in claim 1, in which the gate device is provided for a central portion of the needle.

11. A needlestick prevention device for an injection needle carried by a needle-bearing member of a syringe,
   in which the device is formed as a one-piece moulding and comprises a first part adapted to be attached to the needle-bearing member and a second part providing a shield for the needle and pivotally movable relative to the first part to expose the needle for use,
   the device being adapted to adopt a first position in which the needle is protected for transport of the device prior to use,
   a second position in which the needle is exposed for filling of the syringe and injection,
   a third position in which the needle is protected after filling of the syringe but before injection and
   a fourth position in which the needle is locked in the device following injection,
   the shield having a transport recess and a locking recess connected by a gate device, the arrangement being such that in the third position the needle is in the transport recess and is able to move into the second position, and in the fourth position the needle moves through the gate device into the locking recess, with the gate device preventing movement out of the fourth position,
   wherein the gate device includes two opposing projections formed in the second part to define a partition between the transport recess and a locking recess and a curved path from the transport recess to the locking recess;
   wherein the second part has an extension leading from the transport recess in a direction away from the locking recess to shield the needle when it is in the first and third positions; and
   wherein the extension is a funnel to guide the needle into the transport recess that is open to the exterior of the second part, and wherein the funnel continuously increases in width as it extends outwardly away from the transport recess to the exterior of the second part; and
   wherein the opposing projections extend from respective sides of the funnel.

12. A needlestick prevention device as claimed in claim 1, in which the locking recess is formed in an enlarged portion of the second part.

13. A needlestick prevention device as claimed in claim 1, in which the first part is attached to the needle-bearing member by attachment means providing for the rotation of the needlestick prevention device relative to the needle-bearing member but preventing removal of the device from the needle-bearing member.

14. A needlestick prevention device as claimed in claim 13, in which the attachment means comprises a projection on one of the needle-bearing member and the needlestick prevention device, and a groove on the other.

15. A needlestick prevention device for an injection needle carried by a needle-bearing member of a syringe, in which the device is formed as a one-piece molding and comprises a first part adapted to be attached to the needle-bearing member and a second part providing a shield for the needle and pivotally movable relative to the first part to expose the needle for use, the first and second parts of the device connected by a living hinge, the device being adapted to adopt a first position in which the needle is protected for transport of the device prior to use, a second position in which the needle is exposed for filling of the syringe and injection, a third position in which the needle is protected after filling of the syringe but before injection and a fourth position in which the needle is locked in the device following injection, the shield having a transport recess and a locking recess connected by a gate device, the arrangement being such that in the third position the needle is in the transport recess and is able to move into the second position, and in the fourth position the needle moves through the gate device into the locking recess, with the gate device preventing movement out of the fourth position, wherein the device includes one or more energy dissipation elements provided on a surface of one of the first and second parts, and adapted to contact a corresponding surface on the other of the first and second parts to reduce a kinetic energy of the second part as it is returned to the third position from the second position via the living hinge and before the gate device contacts the needle; and
   wherein the one or more energy dissipation elements include hemispherical bumps.

16. A needlestick prevention device as claimed in claim 15, in which the one or more bumps are provided on the second part, adjacent the hinge.

17. The needlestick prevention device of claim 15, wherein the living hinge is configured to bias the second part from the second position to the third position, and wherein the energy dissipation elements are configured to at least partially reduce the kinetic energy generated by the living hinge.

18. The needlestick prevention device of claim 1, wherein the distal end of the first projection is offset from a distal end of the second projection a first distance along the center line, wherein the distal end of the first projection is offset from the distal end of the second projection a second distance perpendicular to the center line, and wherein the first distance is greater than the second distance.

19. The needlestick prevention device of claim 18, wherein the distal end of the first projection is positioned further from the center line than the distal end of the second projection.

* * * * *